US006747011B1

(12) United States Patent
Zhang

(10) Patent No.: US 6,747,011 B1
(45) Date of Patent: Jun. 8, 2004

(54) ANTITUMOR DRUGS AND METHODS

(75) Inventor: Jennifer H. Zhang, Shanghai (CN)

(73) Assignee: A.P. Group, Inc., Nashua, NH (US)

( * ) Notice: Subject to any disclaimer, the term of this patent is extended or adjusted under 35 U.S.C. 154(b) by 0 days.

(21) Appl. No.: 10/453,921

(22) Filed: Jun. 4, 2003

(51) Int. Cl.[7] .......................... A61K 31/70; C07H 17/08
(52) U.S. Cl. ......................................... 514/28; 536/7.1
(58) Field of Search ............................. 514/28; 536/7.1

(56) References Cited

U.S. PATENT DOCUMENTS

| | | | |
|---|---|---|---|
| 6,548,485 B2 * | 4/2003 | Khosla et al. | ................. 514/28 |
| 2002/0049168 A1 | 4/2002 | Khosla et al. | |
| 2002/0077300 A1 | 6/2002 | Khosla et al. | |

FOREIGN PATENT DOCUMENTS

JP  10-265494 A2  10/1998

OTHER PUBLICATIONS

Wender, P.A.; Isoapoptolidin: Structure and Activity of the Ring–Expanded Isomer of Apoptolidin; Organic Letters; Oct. 1, 2002; 3819–3822; 4–22; American Chemical Society, USA.

Pennington, J.D.; Toward a stable apoptolidin derivative: identification of isoapoptolidin and selective deglycosylation of apoptolidin; Organic Letters; Oct. 1, 2002; 3823–3825; 4–22; American Chemical Society, USA.

Hayakawa, Y.; Structure of Apoptolidin, a Specific Apoptosis Inducer in Transformed Cells; Journal of the American Chemical Society; Mar. 26, 1998; 3524–2525; 120; American Chemical Society; USA.

Salomon, A.R.; Structure–activity relationships within a family of selectively cytotoxic macrolide natural products; Organic Letters; Dec. 9, 2000, (Copyright 2001); 57–59; 3–1; American Chemical Society, USA.

Schuppan, J.; Synthesis of apoptolidinone; Angewandte Chemie, International Edition; Jun. 1, 2001; 2063–2066; 40–11; WILEY–VCH Verlag GmbH; Weinheim, Germany.

Nicolaou, K. C.; Total synthesis of apoptolidin: part 1. Retrosynthetic analysis and construction of building blocks; Angewandte Chemie, International Edition; Oct. 15, 2001, 3849–3854; 40–20; WILEY–VCH Verlag GmbH: Weinheim, Germany.

Nicolaou, K. C.; Total synthesis of apoptolidin; part 2, Coupling of key building blocks and completion of the synthesis; Angewandte Chemie, International Edition; Oct. 15, 2001; 3854–3857; 40–20; WILEY–VCH Verlag GmbH; Weinheim, Germany.

* cited by examiner

*Primary Examiner*—Elli Peselev

(57) ABSTRACT

Derivatives of apoptolidin, including skeletal homologues, are potent and selective apoptosis-inducing agents which, unlike apoptolidin, do not undergo isomerization under physiological conditions. These compounds exhibit antitumor properties, often superior to those of apoptolidin, and as such can be used in the treatment of cancer and other hyperproliferative disorders.

17 Claims, No Drawings

ANTITUMOR DRUGS AND METHODS

BACKGROUND OF THE INVENTION

1. Field of the Invention

The invention relates generally to treatment of cancer and proliferative disorders, and specifically to apoptolidin derivatives and methods of use thereof.

2. Description of Related Art

Agents that can selectively induce apoptosis in cancer cells show great promise for therapeutic use. Compounds capable of being highly specific antitumor agents by selectively leading to tumor cell arrest and apoptosis are desirable.

Apoptolidin, a structurally complex macrolide isolated by Seto and coworkers (Kim, J. W.; Adachi, H.; Shin, Y. K.; Hayakawa, Y.; Seto, H. J. Antibiot., 1997, 50, 628–630; Y. Hayakawa, J. W. Kim, H. Adachi, K. Shin-ya, K. Fujita and H. Seto, J. Am. Chem. Soc., 1998, 120, 3524), has been shown to be a highly selective inducer of apoptosis in certain cancer cell lines, including those derived from human leukemias and melanomas, and colon, renal, central nervous system, and ovarian tumors. Apoptolidin is, however, unstable under alkaline and physiological conditions and readily isomerizes to isoapoptolidin (Wender, P. A., Gulledge, A. V., Jankowski, O. D., Seto, H., Org. Lett., 2002, 4(22), 3819–3822.) This simple-equilibrium interconversion is especially disadvantageous because isoapoptolidin is significantly less potent than apoptolidin. To address this issue and to prepare highly active, stable selective apoptosis-inducing agents, we have focused our efforts on derivatives of apoptolidin which are not prone to isomerization.

BRIEF SUMMARY OF THE INVENTION

In certain embodiments, this invention is directed to derivatives of apoptolidin, including skeletal homologues, which are potent, selective and stable under physiological conditions apoptosis-inducing agents and/or which derivatives do not undergo isomerization to less potent compounds.

In certain embodiments, this invention is directed to compounds of the formula (I) and pharmaceutically acceptable esters, ethers, and/or salts thereof:

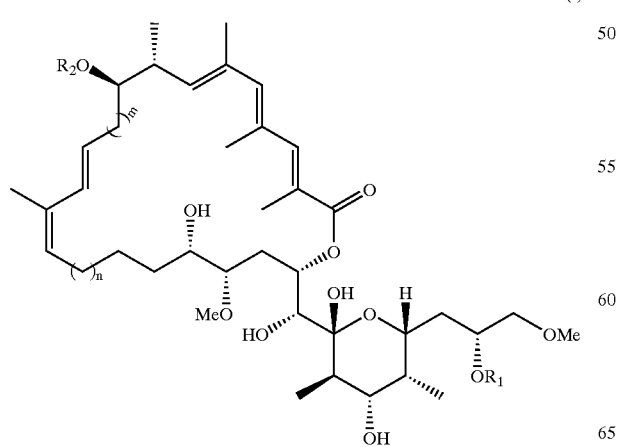

(I)

wherein:

$R_1$ is H, R, or

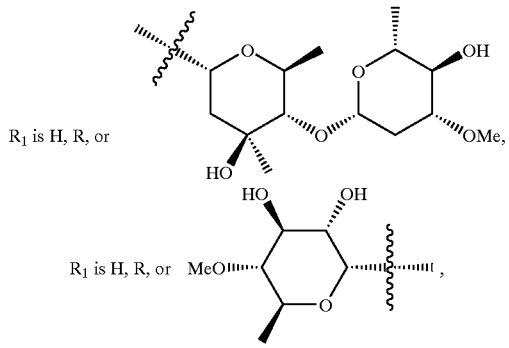

$R_1$ is H, R, or MeO n is an integer from 0 to 6, m is an integer from 0 to 6, except that m≠0 when n=0, and R is a substituted or unsubstituted alkyl, alkenyl, alkynyl, aryl, heterocyclyl, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio.

In certain preferred embodiments, this invention is directed to compounds of the formula (I) and pharmaceutically acceptable esters, ethers, and/or salts thereof, wherein:

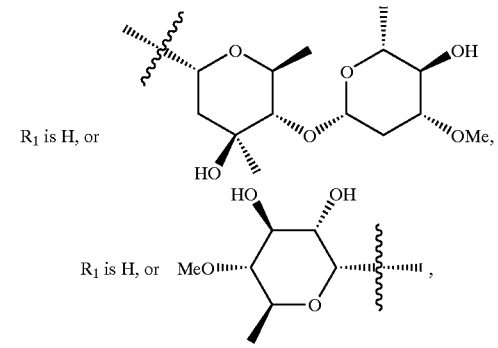

$R_1$ is H, or $R_1$ is H, or MeO n is 0–2, and m is 0–2, except that m≠0 when n=0.

In certain other preferred embodiments, this invention is directed to compounds of the formula (I) and pharmaceutically acceptable esters, ethers, and/or salts thereof, wherein:

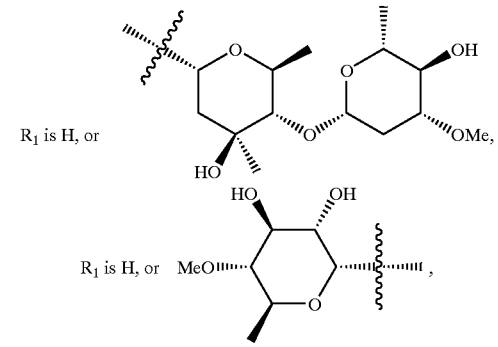

$R_1$ is H, or $R_1$ is H, or MeO n is 1–6 m is 0.

In more preferred embodiments, this invention is directed to compounds of the formula (I) and pharmaceutically acceptable esters, ethers, and/or salts thereof, wherein:

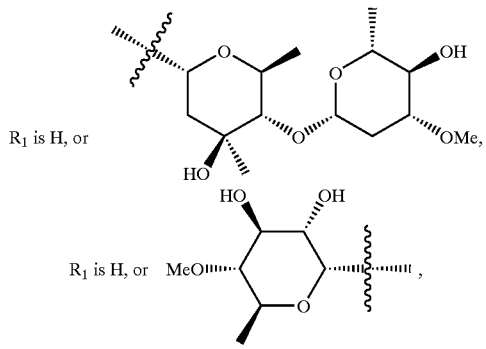

$R_1$ is H, or $R_1$ is H, or n is 1–2, and
m is 0.

In most preferred embodiments, this invention is directed to compounds of the formula (I) and pharmaceutically acceptable esters, ethers, and/or salts thereof, wherein:

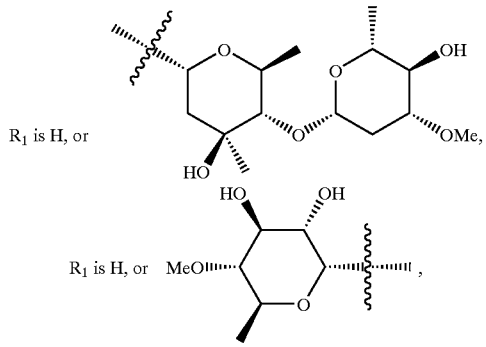

$R_1$ is H, or $R_1$ is H, or n is 1, and
m is 0.

In certain other embodiments, this invention is directed to compounds of the formula (I) and pharmaceutically acceptable esters, ethers, and/or salts thereof, wherein:

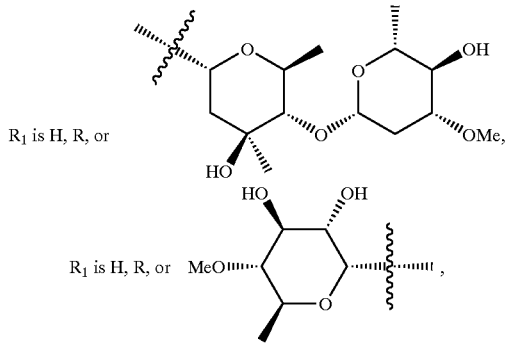

$R_1$ is H, R, or $R_1$ is H, R, or n=0,
m is 1 to 6, and
R is a substituted or unsubstituted alkyl, alkenyl, alkynyl, aryl, heterocyclyl, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio.

In certain more preferred embodiments, this invention is directed to compounds of the formula (I) and pharmaceutically acceptable esters, ethers, and/or salts thereof, wherein:

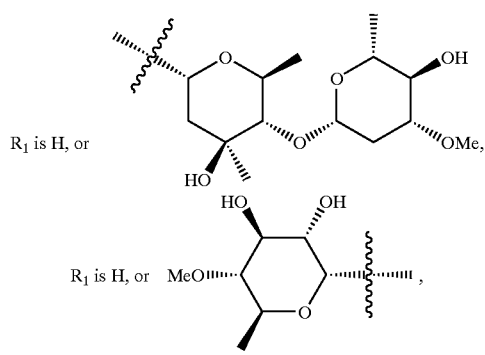

$R_1$ is H, or $R_1$ is H, or n=0, and
m is 1–2.

In most preferred embodiments, this invention is directed to compounds of the formula (I) and pharmaceutically acceptable esters, ethers, and/or salts thereof, wherein:

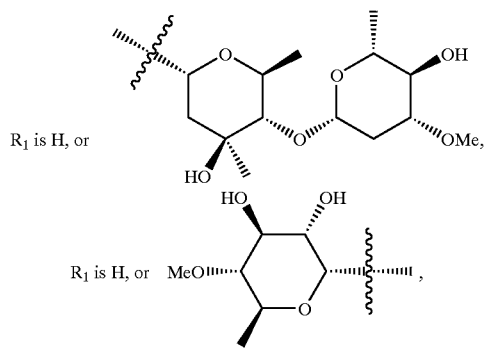

$R_1$ is H, or $R_1$ is H, or n=0, and
m is 1.

In other aspects, the invention is directed to pharmaceutical or veterinary compositions of the compounds of formula (I).

In certain embodiments, this invention is directed to a pharmaceutical composition comprising a pharmaceutically acceptable carrier and as active ingredient the compound of formula I:

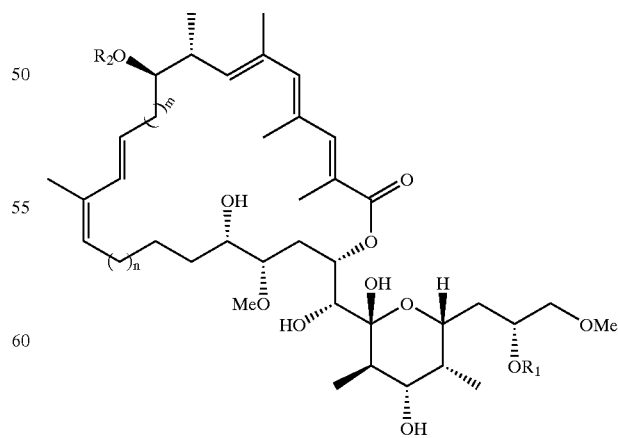

(I)

or pharmaceutically acceptable esters, ethers, and/or salts thereof, wherein:

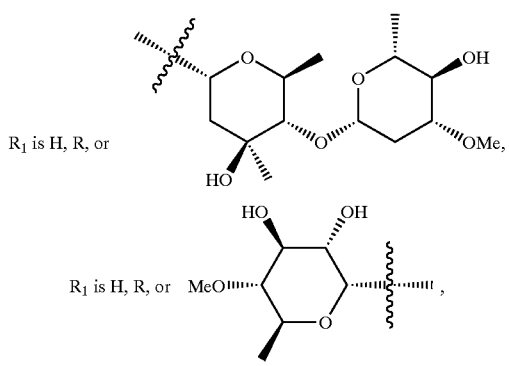

R₁ is H, R, or

R₁ is H, R, or   MeO n is an integer from 0 to 6, m is an integer from 0 to 6, except that m≠0 when n=0, and R is a substituted or unsubstituted alkyl, alkenyl, alkynyl, aryl, heterocyclyl, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio.

In certain preferred embodiments, this invention is directed to a pharmaceutical composition comprising a pharmaceutically acceptable carrier and as active ingredient the compound of formula I or pharmaceutically acceptable esters, ethers, and/or salts thereof, wherein:

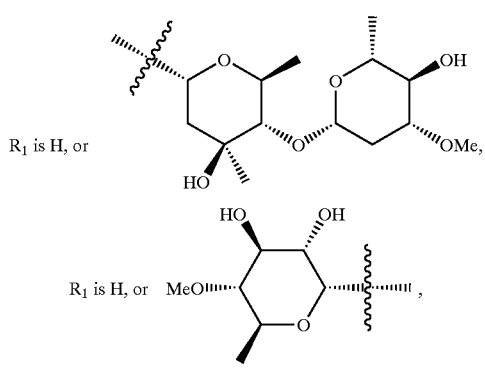

R₁ is H, or

R₁ is H, or   MeO n is 0–2, and m is 0–2, except that m≠0 when n=0.

In certain preferred embodiments, this invention is directed to a pharmaceutical composition comprising a pharmaceutically acceptable carrier and as active ingredient the compound of formula I or pharmaceutically acceptable esters, ethers, and/or salts thereof, wherein:

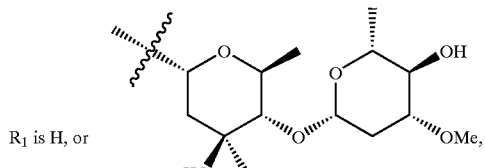

R₁ is H, or

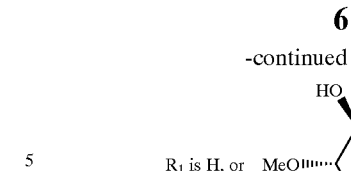

R₁ is H, or   MeO n is 1–6, and m is 0.

In certain more preferred embodiments, this invention is directed to a pharmaceutical composition comprising a pharmaceutically acceptable carrier and as active ingredient the compound of formula I or pharmaceutically acceptable esters, ethers, and/or salts thereof, wherein:

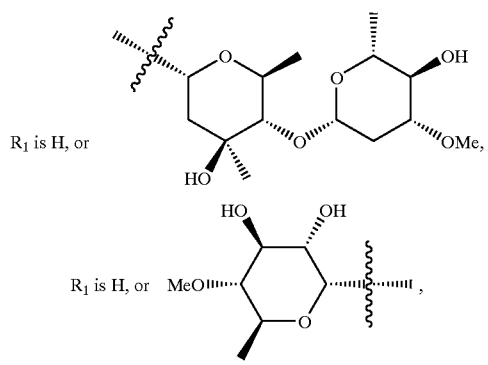

R₁ is H, or

R₁ is H, or   MeO n is 1–2, and m is 0.

In most preferred embodiments, this invention is directed to a pharmaceutical composition comprising a pharmaceutically acceptable carrier and as active ingredient the compound of formula I or pharmaceutically acceptable esters, ethers, and/or salts thereof, wherein:

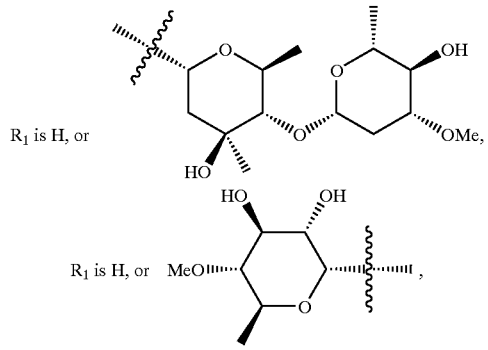

R₁ is H, or

R₁ is H, or   MeO n is 1, and m is 0.

In certain other embodiments, this invention is directed to a pharmaceutical composition comprising a pharmaceutically acceptable carrier and as active ingredient the compound of formula I or pharmaceutically acceptable esters, ethers, and/or salts thereof, wherein:

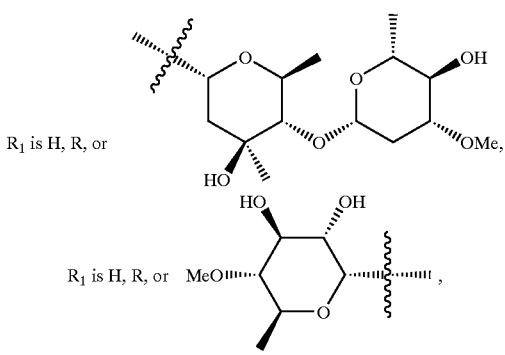

R$_1$ is H, R, or

R$_1$ is H, R, or MeO n=0, m is 1 to 6, and

R is a substituted or unsubstituted alkyl, alkenyl, alkynyl, aryl, heterocyclyl, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio.

In certain more preferred embodiments, this invention is directed to a pharmaceutical composition comprising a pharmaceutically acceptable carrier and as active ingredient the compound of formula I or pharmaceutically acceptable esters, ethers, and/or salts thereof, wherein:

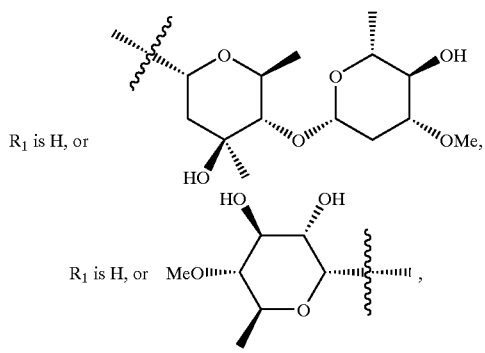

R$_1$ is H, or

R$_1$ is H, or MeO n=0, and m is 1–2.

In most preferred embodiments, this invention is directed to a pharmaceutical composition comprising a pharmaceutically acceptable carrier and as active ingredient the compound of formula I or pharmaceutically acceptable esters, ethers, and/or salts thereof, wherein:

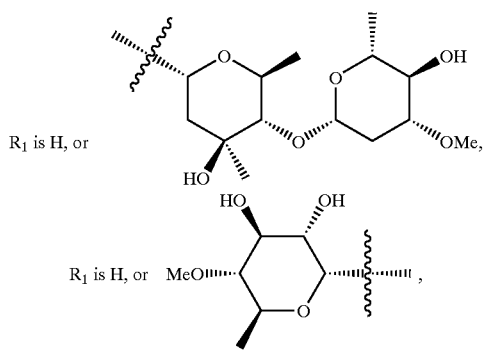

R$_1$ is H, or

R$_1$ is H, or MeO n=0, and m is 1.

In other aspects, the invention is directed to methods to treat hyperproliferative disorders and tumors and cancers by administering the compound of formula (I) or a pharmaceutical composition thereof to a patient in the need of such treatment. "Treatment" includes both therapeutic and prophylactic effects.

In certain embodiments, this invention is directed to a method of treatment of a cancer in a patient, which method comprises administering to a patient in need of such treatment a therapeutically effective amount of the compounds or pharmaceutical compositions disclosed herein.

DETAILED DESCRIPTION OF THE INVENTION

This invention relates to derivatives of apoptolidin, including skeletal homologues, which are potent, selective and stable under physiological conditions apoptosis-inducing agents and/or which derivatives do not undergo isomerization to less potent compounds. Further, this invention relates to pharmaceutical compositions comprising compounds described herein and to their use as therapeutic agents, particularly in the treatment of cancer and cell proliferative disorders.

More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma.

Compounds of formula (I) may be used in combination with known anticancer agents or sequentially with known anticancer agents when a combination formulation is inappropriate. Anticancer agents include, but are not limited to actinomycin D, amsacrine, camptothecins, carboplatin, cisplatin, colchicine, cyclosporin A, cyclophosphamide, doxorubicin, etoposide, etoposide, interferon, mitoxantrone, phenothiazines, vinblastine, vincristine, taxol, tenipaside, and thioxantheres.

Compounds of formula (I) may be used in combination with known antiviral agents or sequentially with known antiviral agents when a combination formulation is inappropriate. Antiviral agents include, but are not limited to Cytovene, Ganciclovir, trisodium phosphonoformate, Ribavirin, d4T, ddI, AZT, and acyclovir.

The compounds of this invention, as modulators of apoptosis, are be useful in the treatment of cancer, viral infections, prevention of AIDS development in HIV-infected individuals, autoimmune diseases and neurodegenerative disorders. Furthermore, the compounds of this invention could be useful in inhibiting tumor angiogenesis and metastasis.

Medical Definitions

For convenience, certain terms employed in the specification, examples, and appended claims are collected here.

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which will be limited only by the appended claims.

The term "hyperproliferative disorders" refers to excess cell proliferation, relative to that occurring with the same type of cell in the general population and/or the same type of cell obtained from a patient at an earlier time. The term denotes malignant as well as non-malignant cell populations. Such disorders have an excess cell proliferation of one or more subsets of cells, which often appear to differ from the surrounding tissue both morphologically and genotypically. The excess cell proliferation can be determined by reference to the general population and/or by reference to a particular patient, e.g. at an earlier point in the patient's life. Hyperproliferative cell disorders can occur in different types of animals and in humans, and produce different physical manifestations depending upon the affected cells.

Hyperproliferative cell disorders include cancers; blood vessel proliferative disorders such as restenosis, atherosclerosis, in-stent stenosis, vascular graft restenosis, etc.; fibrotic disorders; psoriasis; inflammatory disorders, e.g. arthritis, etc.; glomerular nephritis; endometriosis; macular degenerative disorders; benign growth disorders such as prostate enlargement and lipomas; and autoimmune disorders. Cancers are of particular interest, including leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, hematopoietic cancers, head and neck cancers, and nervous system cancers, benign lesions such as papillomas, and the like.

The term "inhibit" or "inhibiting" means decreasing tumor cell growth rate from the rate which would occur without treatment, and/or causing tumor mass to decrease. Inhibiting also includes causing a complete regression of the tumor. Thus, the present analogs can either be cytostatic or cytotoxic to tumor cells.

The term "therapeutically effective amount" refers to the amount which, when administered to an animal for treating a disease, is sufficient to effect such treatment for the disease.

The term "treating" or "treatment" of a disease in a mammal includes: (1) preventing the disease from occurring in a mammal which may be predisposed to the disease but does not yet experience or display symptoms of the disease, (2) inhibiting the disease, i.e., arresting its development, or (3) relieving symptoms of the disease, i.e., causing regression of the disease.

An "effective amount" of, e.g., an antitumor agent, with respect to the subject method of treatment, refers to an amount of the antagonist in a preparation which, when applied as part of a desired dosage regimen brings about, e.g., a change in the rate of cell proliferation and/or the state of differentiation of a cell and/or rate of survival of a cell according to clinically acceptable standards for the disorder to be treated or the cosmetic purpose.

A "patient" or "subject" to be treated by the subject method can mean either a human or non-human animal.

The "growth state" of a cell refers to the rate of proliferation of the cell and/or the state of differentiation of the cell.

The terms "epithelia", "epithelial" and "epithelium" refer to the cellular covering of internal and external body surfaces (cutaneous, mucous and serous), including the glands and other structures derived therefrom, e.g., corneal, esophegeal, epidermal, and hair follicle epithelial cells. Other exemplary epithlelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, like that which is characteristically found lining hollow organs that are subject to great mechanical change due to contraction and distention, e.g. tissue which represents a transition between stratified squamous and columnar epithelium.

The term "epithelialization" refers to healing by the growth of epithelial tissue over a denuded surface.

The term "skin" refers to the outer protective covering of the body, consisting of the corium and the epidermis and is understood to include sweat and sebaceous glands, as well as hair follicle structures. Throughout the present application, the adjective "cutaneous" may be used, and should be understood to refer generally to attributes of the skin, as appropriate to the context in which they are used.

The term "epidermis" refers to the outermost and nonvascular layer of the skin, derived from the embryonic encoder, varying in thickness from 0.07–1.4 nun. On the palmar and plantar surfaces it comprises, from within outward, five layers; basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent.

As used herein, "proliferating" and "proliferation" refer to cells undergoing mitosis. Throughout this application, the term "proliferative disorder" refers to any disease/disorder marked by unwanted or aberrant proliferation of tissue.

Chemical Definitions

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., C1–C30 for straight chain, C3–C30 for branched chain), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls," the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted allyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g. an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

The term "heteroatom" as used herein means an atom of any element other than carbon or hydrogen. Preferred heteroatoms are boron, nitrogen, oxygen, phosphorus, sulfur and selenium.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

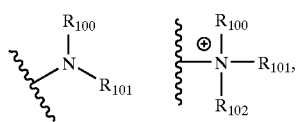

wherein $R_{100}$, $R_{101}$ and $R_{102}$ each independently represent a hydrogen, an alkyl, an alkenyl, —$(CH_2)_m$—$R_{110}$, or $R_{100}$ and $R_{101}$ taken together with the N atom to which they are attached complete a heterocycle having from 4 to 8 atoms in the ring structure; $R_{110}$ represents an aryl, a cycloalkyl, a cycloalkenyl, a heterocycle or a polycycle; and m is zero or an integer in the range of 1 to 8. In preferred embodiments, only one of $R_{100}$ or $R_{101}$ can be a carbonyl, e.g., $R_{100}$, $R_{101}$ and the nitrogen together do not form an imide. In even more preferred embodiments, $R_{100}$ and $R_{101}$ (and optionally $R_{102}$) each independently represent a hydrogen, an alkyl, an alkenyl, or $-(CH_2)_m-R_{110}$. Thus, the term "alkylamine" as used herein means an amine group, as defined above, having a substituted or unsubstituted alkyl attached thereto, i.e., at least one of $R_{100}$ and $R_{101}$ is an alkyl group.

The term "acylamino" is art-recognized and refers to a moiety that can be represented by the general formula:

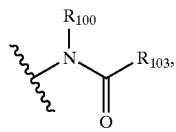

wherein $R_{100}$ as defined above, and $R_{103}$ represents a hydrogen, an alkyl, an alkenyl or $-(CH_2)_m-R_{110}$, wherein m and $R_{110}$ are as defined above.

The term "amido" is art recognized as an amino-substituted carbonyl and includes a moiety that can be represented by the general formula:

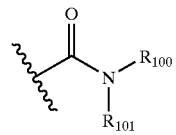

wherein $R_{100}$, $R_{110}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of $-S$-alkyl, $-S$-alkenyl, $-S$-alkynyl, and $-S-(CH_2)_m-R_{110}$, wherein m and $R_{110}$ are defined above. Representative alkylthio groups include methylthio, ethyl thio, and the like.

The term "carbonyl" is art recognized and includes such moieties as can be represented by the general formula:

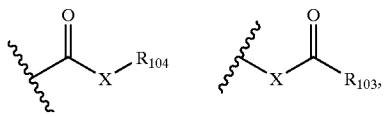

wherein X is a bond or represents an oxygen or a sulfur, and $R_{104}$ represents a hydrogen, an alkyl, an alkenyl, $-(CH_2)_m-R_{110}$ or a pharmaceutically acceptable salt, $R_{103}$ represents a hydrogen, an alkyl, an alkenyl or $-(CH_2)_m-R_{110}$, where m and $R_{110}$ are as defined above. Where X is an oxygen and $R_{104}$ or $R_{103}$ is not hydrogen, the formula represents an "ester". Where X is an oxygen, and $R_{104}$ is as defined above, the moiety is referred to herein as a carboxyl group, and particularly when $R_{104}$ is a hydrogen, the formula represents a "carboxylic acid". Where X is an oxygen, and $R_{103}$ is a hydrogen, the formula represents a "formate". In general, where the oxygen atom of the above formula is replaced by sulfur, the formula represents a "thiolcarbonyl" group. Where X is a sulfur and $R_{104}$ or $R_{103}$ is not hydrogen, the formula represents a "thiolester." Where X is a sulfur and $R_{104}$ is hydrogen, the formula represents a "thiolcarboxylic acid." Where X is a sulfur and R11' is hydrogen, the formula represents a "thiolformate." On the other hand, where X is a bond, and $R_{104}$ is not hydrogen, the above formula represents a "ketone" group. Where X is a bond, and $R_{104}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of $-O$-alkyl, $-O$-alkenyl, $-O$-alkynyl, $-O-(CH_2)_m-R_{110}$, where m and $R_{110}$ are described above.

The term "sulfonate" is art recognized and includes a moiety that can be represented by the general formula:

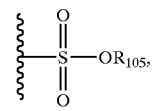

in which $R_{105}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutane-sulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "sulfate" is art recognized and includes a moiety that can be represented by the general formula:

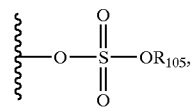

in which $R_{105}$ is as defined above.

The term "sulfonamido" is art recognized and includes a moiety that can be represented by the general formula:

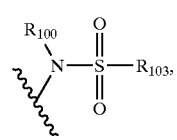

in which $R_{100}$ and $R_{103}$ are as defined above.

The term "sulfamoyl" is art-recognized and includes a moiety that can be represented by the general formula:

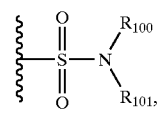

in which $R_{100}$ and $R_{101}$ are as defined above.

The terms "sulfoxido" or "sulfinyl", as used herein, refers to a moiety that can be represented by the general formula:

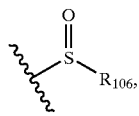

in which $R_{106}$ is selected from the group consisting of hydrogen, alkyl, alkenyl, alkynyl, cycloalkyl, heterocyclyl, aralkyl, or aryl.

A "phosphoryl" can in general be represented by the formula:

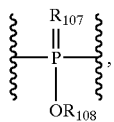

wherein $R_{107}$ represented S or O, and $R_{108}$ represents hydrogen, a lower alkyl or an aryl. When used to substitute, e.g. an alkyl, the phosphoryl group of the phosphorylalkyl can be represented by the general formula:

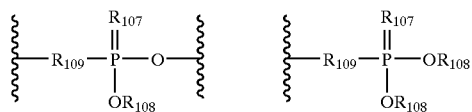

wherein $R_{107}$ represented S or O, and each $R_{108}$ independently represents hydrogen, a lower alkyl or an aryl, $R_{109}$ represents O, S or N. When $R_{107}$ is an S, the phosphoryl moiety is a "phosphorothioate".

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_{110}$, m and $R_{110}$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

Certain compounds of the present invention may exist in particular geometric or stereoisomeric forms. "Stereoisomers" are compounds that have the same sequence of covalent bonds and differ in the relative disposition of their atoms in space. Stereoisomers fall within two broad classes: optical isomers and geometric isomers. The present invention contemplates all such compounds, including cis- and trans-isomers, R- and S-enantiomers, diastereomers, (D)isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g. the ability to selectively induce apoptosis in certain cancer cell lines), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a (C1–C6)alkyl, phenyl or benzyl ester or amide; or as an a-methylbenzyl amide). Other suitable amino and carboxy protecting groups are known to those skilled in the art (See for example, T. W. Greene, Protecting Groups In Organic Synthesis; Wiley: N.Y., 1981, and references cited therein). An amino acid can be linked to the remainder of a compound of formula I through the carboxy terminus, the amino terminus, or through any other convenient point of attachment, such as, for example, through the sulfur of cysteine.

The term "peptide" describes a sequence of 2 to 25 amino acids (e.g. as defined hereinabove) or peptidyl residues. The sequence may be linear or cyclic. For example, a cyclic peptide can be prepared or may result from the formation of disulfide bridges between two cysteine residues in a sequence. A peptide can be linked to the remainder of a compound through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2.sup.nd ed.; Wiley: N.Y., 1991).

The term "prodrug" is intended to encompass compounds which, under physiological conditions, are converted into the therapeutically active agents of the present invention. A common method for making a prodrug is to select moieties which are hydrolyzed under physiological conditions to provide the desired. In other embodiments, the prodrug is converted by an enzymatic activity of the host animal.

A list of many of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

Pharmaceutical Compositions

While it is possible for a compound of the present invention to be administered alone, it is preferable to administer the compound as a pharmaceutical formulation (composition). The antitumor agents according to the invention may be formulated for administration in any convenient way for use in human or veterinary medicine.

Thus, another aspect of the present invention provides pharmaceutically acceptable compositions comprising a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water.

The phrase "therapeutically-effective amount" as used herein means that amount of a compound, material, or composition comprising a compound of the present invention which is effective for producing some desired therapeutic effect by inducing apoptosis of cancer cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present antitumor agents may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1–19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The tern "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form wvith a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al. supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like: (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, i.e. particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or salicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

It is known that sterols, such as cholesterol, will form complexes with cyclodextrins. Thus, in preferred embodiments, where the inhibitor is a steroidal alkaloid, it may be formulated with cyclodextrins, such as α-, beta- and γ-cyclodextrin, dimethyl β-cyclodextrin and 2-hydroxypropyl-β-cyclodextrin.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active hedgehog antagonist.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the hedgehog antagonists in the proper medium. Absorption enhancers can also be used to increase the flux of the hedgehog antagonists across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition". W. H. Freedman and CO., San Francisco, U.S.A., 1969 or "Livestock Feeds and Feeding" O and B books. Corvallis, Oreg., U.S.A., 1977).

Administration

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration," and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular apoptosis-inducing agent employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Synthetic Schemes

Compounds of the present invention may be prepared by general routes applicable to the synthesis of apoptolidin. See, e.g., Scheidt, K. A., Ph.D. Thesis, 1999, Department of Chemistry Indiana University; Nicolaou, K. C., Li Yiwei, Weyerhausen, B., Wei, H., Chem. Comm., 2000, 4, 307–308; Misske, A. M., Hoffmann, H. M. R., Chem. Eur. J., 2000, 6(18), 3313–3320; Schuppan, J., Ziemer, B., Koert, U., Tetrahedron Lett., 1999, 41, 621–624; Schuppan, J., Wehlan, H., Keiper, S., Koert, U., Angew. Chem. Int. Ed., 2001, 40(11), 2063–2066; Nicolaou, K. C., Li, Y., Fylaktakidou, K. C., Mitchell, H. J., Wei, H.-X., Weyershausen, B., Angew. Chem. Int. Ed., 2001, 40(20), 3849–3854; Nicolaou, K. C., Li, Y., Fylaktakidou, K. C., Mitchell, H. J., Sugita, K., Angew. Chem. Int. Ed., 2001, 40(20), 3854–3857; Toshima, K., Arita, T., Kato, K., Tanaka, D., Matsumura, S., Tetrahedron Lett., 2001, 42, 8873–8876; Chen, Y., Evarts, J. B., Torres, E., Fuchs, P. L., Org. Lett., 2002, 4(21), 3571–3574.

Specifically, the synthesis of compounds of formula I (wherein n=0–6 and m=0–6) can be accomplished using the approach of Nicolaou as outlined below.

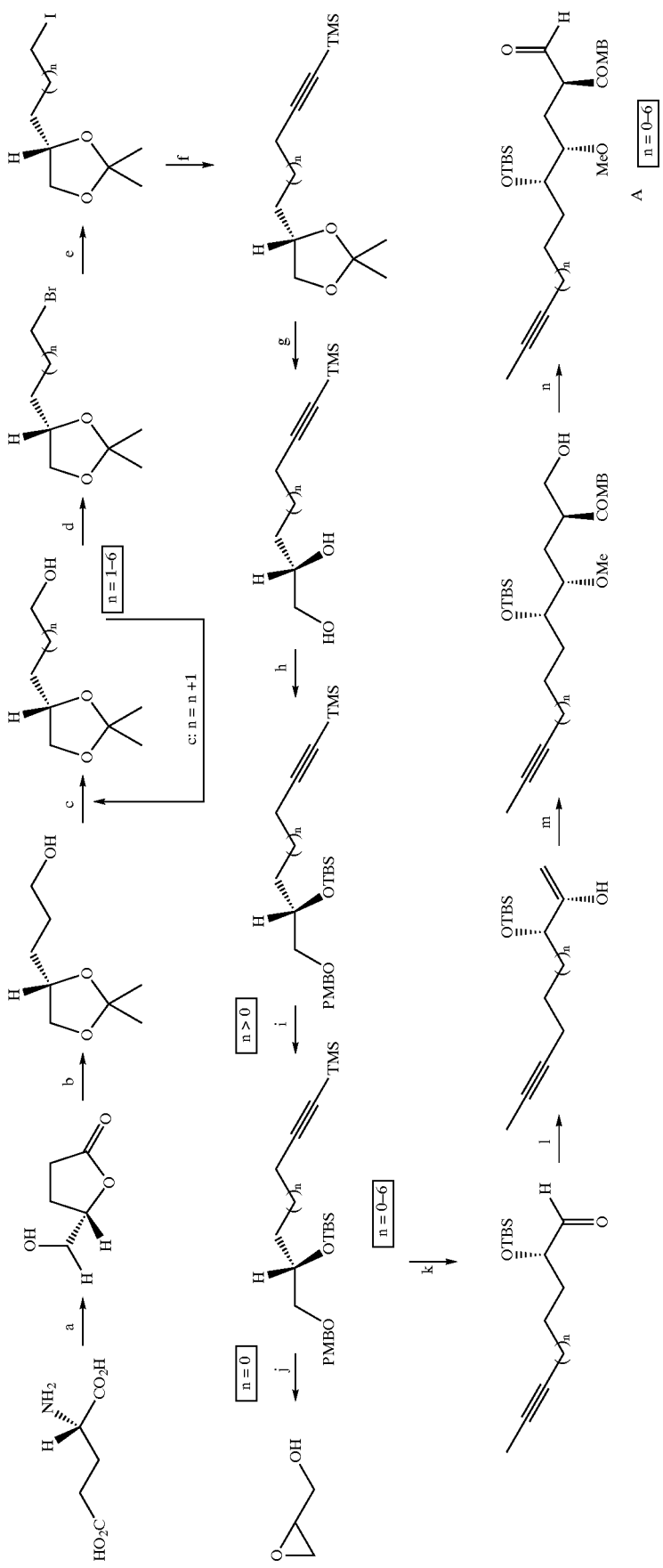

The synthesis begins with the preparation of the acetylenic precursor A. In step a, L-glutamic acid is converted by sodium nitrite/sulfuric acid solution, followed by borane-dimethyl sulfite complex to (S)-(+)-5-hydroxymethyl-dihydrofuran-2-one (Larcheveque, M., Lalande, J., Tetrahedron, 1984, 40(6), 1061–1065). In step b, (S)-(+)-5-hydroxymethyl-dihydrofuran-2-one is converted with 2,2-dimethoxypropane in methanol in the presence of Amberlyst 15, followed by LAH reduction, to (S)-(−)-3-(2,2-Dimethyl-[1,3]dioxolan-4-yl)-propan-1-ol (Larcheveque, M., Lalande, J., Tetrahedron, 1984, 40(6), 1061–1065). In step c, the three membered exocyclic carbon chain may extended to a required length, one carbon atom at a time, via the following reaction sequence: (1) oxidation to the corresponding aldehyde (TPAP, NMO), (2) Wittig olefination to the corresponding α-olefin, and (3) hydroboration to the corresponding terminal alcohol. For n=1, step c is skipped, for n=2, step c is executed once, for n=3 step c is executed twice, etc.; overall, for n=i, step c is executed i-1 times. In step d, the primary alcohol is converted to the primary bromide with $PPh_3$, $CBr_4$, $Et_3N$, in dichloromethane (Yang, W-Q., Kitahara, T., Tetrahedron Lett., 1999, 40, 7827–7830). In step e, the primary bromide is converted to primary iodide with $PPh_3$, $I_2$, in $CH_3CN$, $Et_2O$ (Yang, W-Q., Kitahara, T., Tetrahedron, 2000, 56, 1451 –1461). In step f, the primary iodide is exposed to TMSC≡CH, n-BuLi, THF, HMPA, resulting a TMS-protected terminal acetylene (Yang, W-Q., Kitahara, T., Tetrahedron, 2000, 56, 1451–1461). In step g, the dioxolane moiety is removed with AcOH, $H_2O$ resulting in a 1,2-diol (Yang, W-Q., Kitahara, T., Tetrahedron, 2000, 56, 1451–1461). In step h, the primary alcohol is converted with PMBCl to the corresponding PMB-ether and the secondary alcohol is converted with TBSCl to the corresponding TBS-ether. For n>0, in step i, the terminal TMS-acetylide is deprotected and methylated to the corresponding internal alkyne. For, n=0, the corresponding intermediate is prepared according to the approach of Nicolaou (Nicolaou, K. C., Li, Y., Fylaktakidou, K. C., Mitchell, H. J., Wei, H.-X., Weyershausen, B., Angew. Chem. Int. Ed., 2001, 40(20), 3849–3854). In step k, the PMB group is removed with DDQ, and the primary alcohol is oxidized to the corresponding aldehyde with TPAP, NMO. In step l, reaction of the aldehyde with (+)-allyldiisopinocampheylborane produced the desired secondary alcohol stereoselectively (>10:1 selectivity). In step m, the secondary alcohol was protected with MeOTf, as the methyl ether; the terminal olefin was exposed to Sharpless asymmetric dihydroxylation conditions providing the corresponding diol (6:1 ratio of diastereomers), which was protected with 3,4-dimethoxybenzaldehyde, CSA, following opened regioselectively with DIBAL-H. In step n, the resultant primary alcohol was oxidized up to the corresponding aldehyde with $SO_3$-py, DMSO.

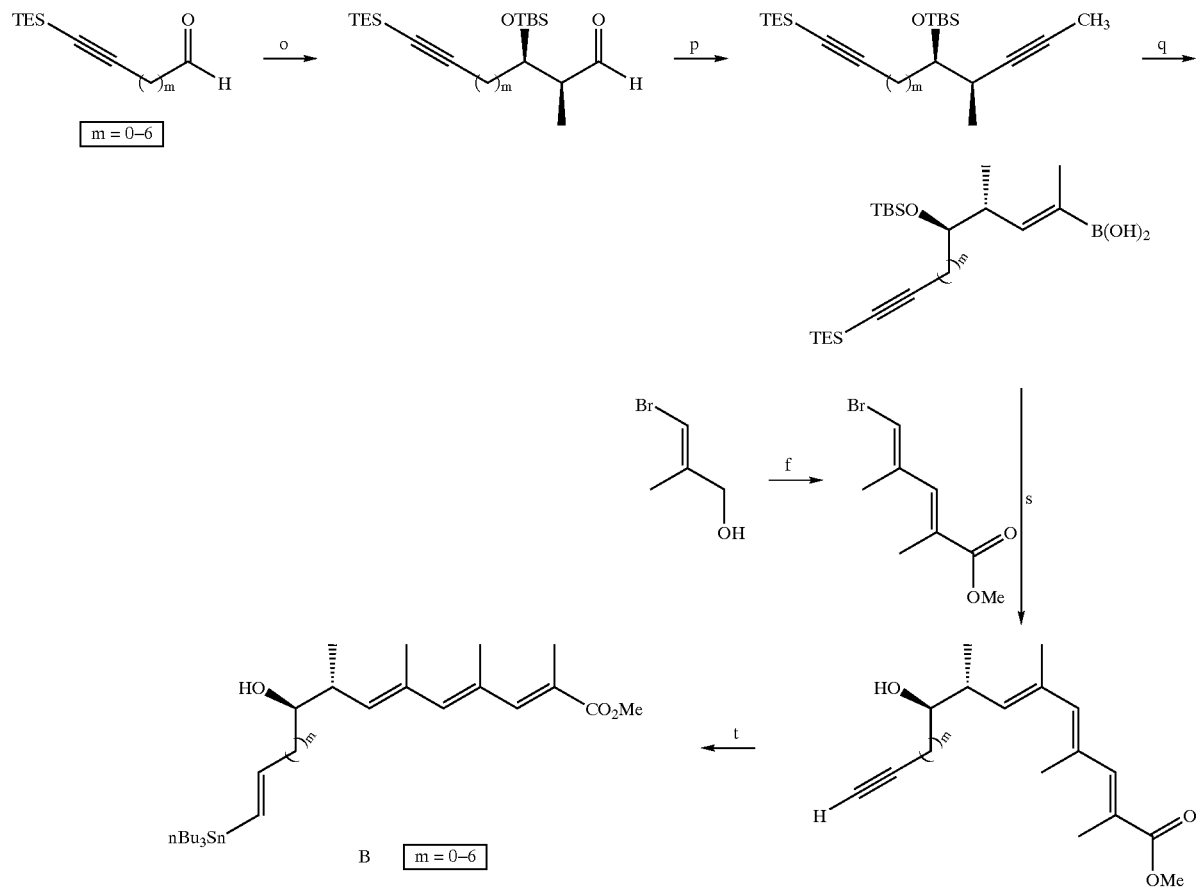

The synthesis continued with the preparation of acetylenic precursor B, as outlined above. In step o, terminal acetylenic aldehyde (m=0: Nicolaou, K. C., Li, Y., Fylaktakidou, K. C., Mitchell, H. J., Wei, H.-X., Weyershausen, B., Angew. Chem. Int. Ed., 2001, 40(20), 3849–3854; m=2: Thompson, C. F., Jamison, T. F., Jacobsen, E. N., JACS, 2001, 123, 9974–9983; m=3: U.S. Pat. No. 4,994,486; in general, m=i precursors can be prepared by chain extension of the m=i-1 precursors by the following reaction sequence: (1) LAH reduction, (2) conversion of the primary alcohol to the corresponding bromide, (3) conversion of the primary bromide to the corresponding Grygnard reagent, (4) addition of the resultant Grygnard reagent to formaldehyde or its equivalent (e.g., paraformaldehyde)) is treated with (Z)-(+)-crotyldiisopinocampheyl borane, the resultant alcohol is protected as a TBS ether, and the olefinic bond is ozonalyzed to yield the corresponding aldehyde. In step p, the resultant aldehyde is treated with Bestmann's reagent to afford diacetylene, the terminal alkyne of which is methylated with n-BuLi, MeI. In step q, the resultant diacetylene is regio- and stereoselectively hydroborated with catecholborane and catalytic amounts of 9-BBN, followed by hydrolysis to the corresponding vinylic boronic acid. In step s, a Suzuki type coupling of the vinylic boronic acid with vinyl bromide (prepared in step r, by one pot reaction of allylic alcohol with $MnO_2$ and $MeC(=PPh_3)CO_2Et$ and subsequent ester exchange with LiOH, followed by $CH_2N_2$), followed by desilylation with TBAF yielded the desired terminal alkyne. In step t, the terminal alkyne was regio- and stereoselectively hydrostannylated with $nBu_3SnH$, cat. $(PPh_3)_2PdCl_2$ to give the desired precursor B.

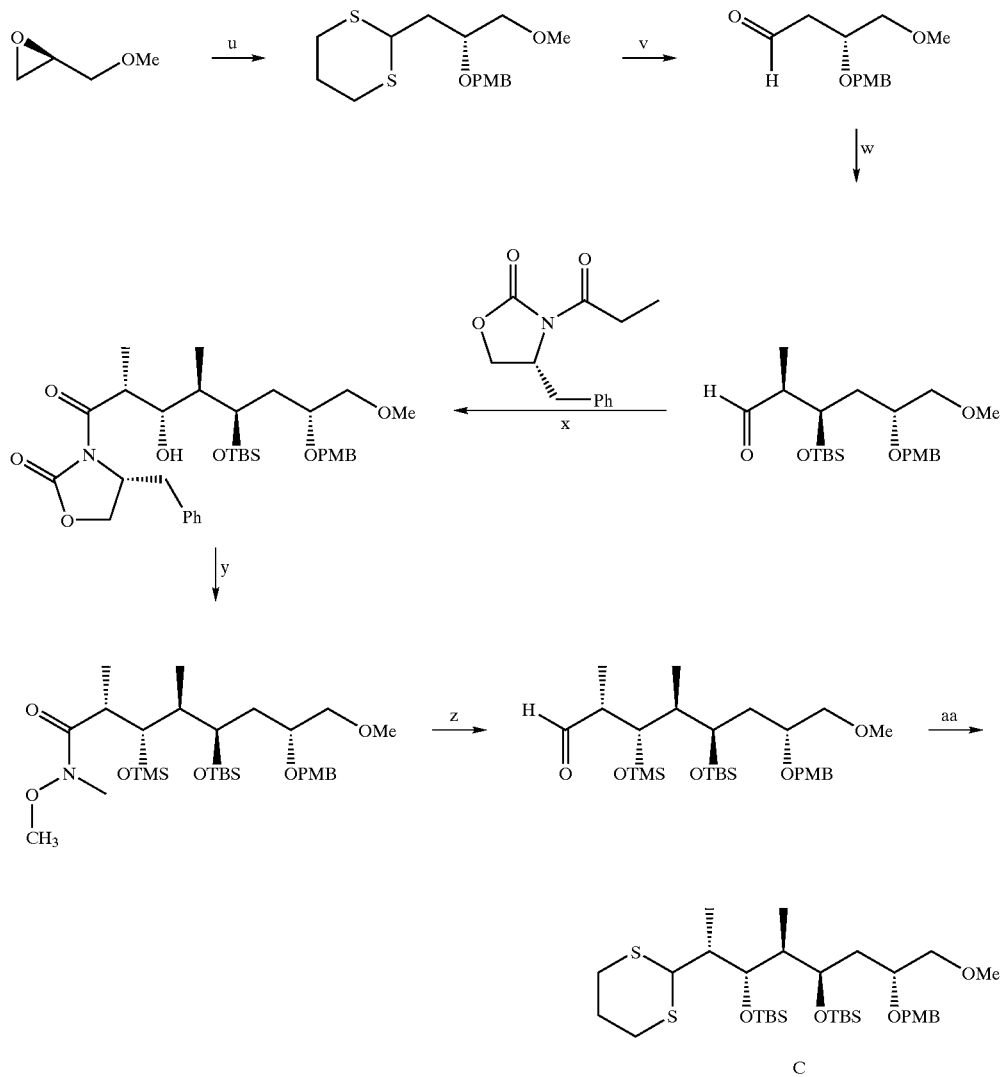

The synthesis continued with the preparation of the multi-ether precursor C, as outlined above (Nicolaou, K. C., Li, Y., Fylaktakidou, K. C., Mitchell, H. J., Wei, H.-X., Weyershausen, B., Angew. Chem. Int. Ed., 2001, 40(20), 3849–3854). In step u, (−)-glycidol methyl ether was ring-opened with the anion of 1,3-dithiane to afford the corresponding secondary alcohol, which was protected as the PMB ether by the treatment with PMBCl in the presence of NaH and cat. $nBu_4NI$. In step v, the dithiane was deprotected (MeI, $K_2CO_3$). In step w, the resultant aldehyde was treated with (Z)-(+)-crotyldiisopinocampheyl borane in the presence of $BF_3$-$Et_2O$ to afford the corresponding hydroxyl olefin, which was then protected with TBS-OTf and cleaved upon exposure to $NaIO_4$, cat. $OsO_4$ to yield the corresponding aldehyde. In step x, the aldehyde was reacted with boron enolate derived from Evan's chiral auxiliary and $nBu_2BOTf$ to furnish the corresponding syn-aldol product. In step y, the syn-aldol product was converted to Weinreb amide upon treatment with MeNH(OMe)-HCl and $AlMe_3$, and the free hydroxyl group was protected with TMSOTf to the corresponding TMS-ether. In step z, DIBAL-H reduction converted the Weinreb amide to the corresponding aldehyde. And finally, in step aa, the aldehyde was converted to the dithiane moiety upon treatment with $HS(CH_2)_3SH$, $BF_3$-$Et_2O$ to yield the desired fragment C.

to the aldehyde fragment A to afford a coupling product as a 1.5:1 mixture of diastereomers. The diastereomers were separated and brought forward in parallel and the undesired diastereomer was converted into the desired one at a later stage. Thus, the silyl groups were removed with TBAF, and the dithiane moiety was removed by exposure to $PhI(CF_3-CO_2)_2$ to give the corresponding lactols, which were resilylated with TBS-OTf. At this stage, NEO studies revealed that the major diastereomer was the desired one. In step ac, both diastereomers were treated with trimethyl orthoacetate in the presence of PPTS to yield the corresponding orthoesters. In step ad, the orthoesters were converted to the corresponding vinyl iodides as a ca. 5:1 mixture of the regioisomers via hydrozirconation and Zr-I exchange ($[Cp]_2$ZrClH; $I_2$). The undesired minor methyl glycoside diastereomer was converted to the desired stereoisomer by oxidation with DMP followed by reduction with $NaBH_4$. Both PMB and DMB protecting groups were removed with DDQ

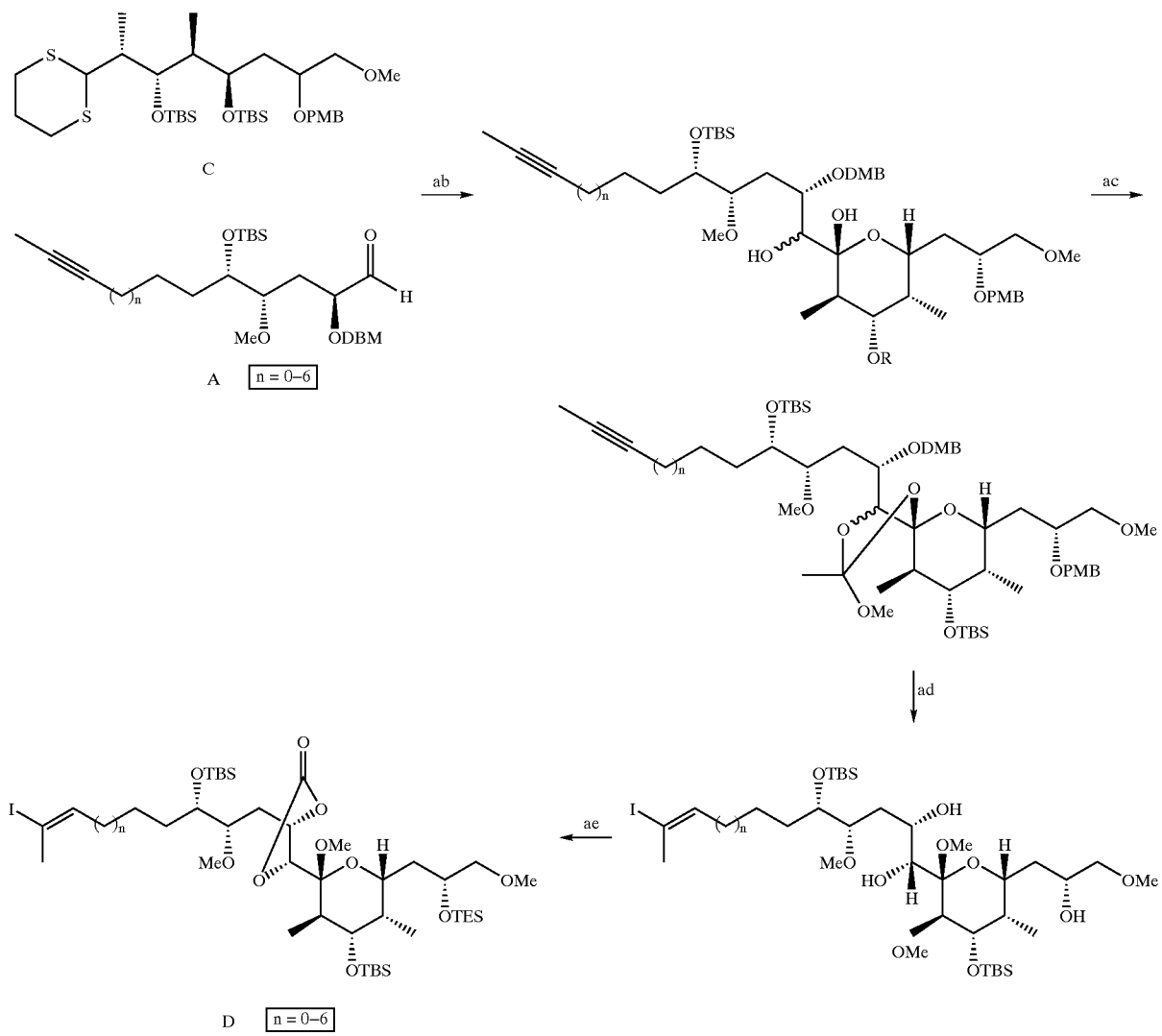

and LiOH resulting in the corresponding desired triol. In step ae, the adjacent free hydroxyl groups were converted to the corresponding carbonate with triphosgene/pyridine, and the third hydroxyl group was silylated with TESOTf/2,6-lutidine yielding fragment D.

The synthesis continued with brining fragments A and C together as outlined above (Nicolaou, K. C., Li, Y., Fylaktakidou, K. C., Mitchell, H. J., Sugita, K., Angew. Chem. Int. Ed., 2001, 40(20), 3854–3857). In step ab, the dithiane fragment C was converted to its anion with nBuLi and added

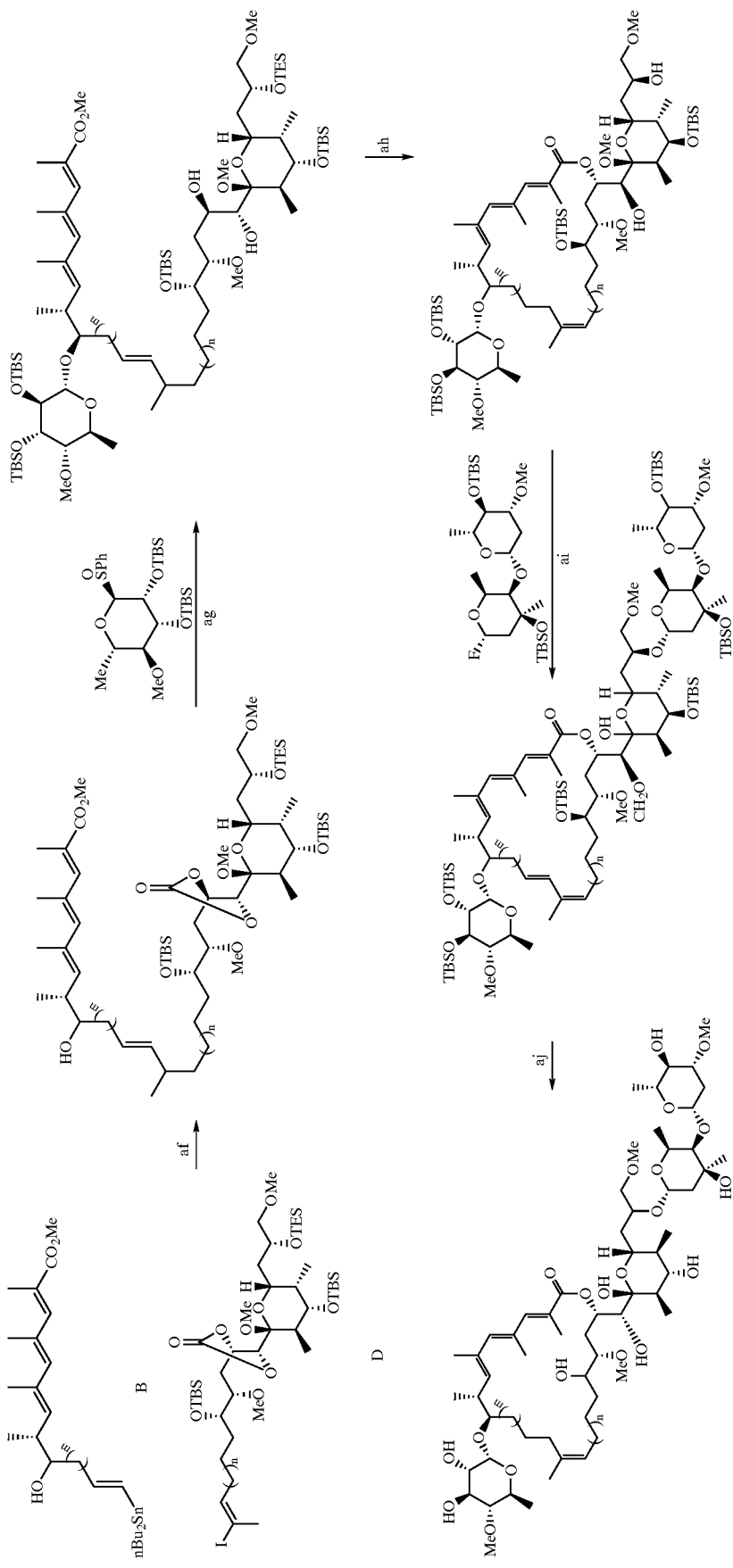

In step a fragments B and D were coupled via Stille coupling in the presence of [Pd(CH₃CN)₂Cl₂]. In step ag, the resultant vinyl alcohol, was coupled with a carbohydrate donor (Kahne, D., Walker, S., Cheng, Y., Engen, D. V., JACS, 1989, 111, 6881–6882) to give the corresponding α-glycoside. Both the carbonate moiety and methyl ester group were then cleaved with KOH to give the resultant dihydroxy carboxylic acid. In step ah, Yamaguchi macrolactonization was carried out with excess 2,4,6-trichlorobenzoyl chloride and Et₃N, followed by excess 4-DMAP. The remaining hydroxy group was protected with a chloroacetyl group and the TES group was selectively removed with PPTS in MeOH. In step ai, the resultant hydroxy compound was attached to the glycosyl fluoride (Nicolaou, K. C., Li, Y., Fylaktakidou, K. C., Mitchell, H. J., Wei, H.-X., Weyershausen, B., Angew. Chem. Int. Ed., 2001, 40(20), 3849–3854) via SnCl₂-induced coupling. Finally, global deprotection was accomplished in step aj with HF-pyr to remove the silyl groups, followed by Et₃N in MeOH to remove the chloroacetyl group, and TsOH in THF/H₂O to cleave the methyl glycoside.

Obviously, numerous modifications and variations of the present invention are possible in light of the above teachings. It is therefore to be understood that within the scope of the appended claims, the invention may be practiced otherwise than as specifically described herein.

EXAMPLES

EXAMPLE 1

Compound of Formula I ($R_1=$

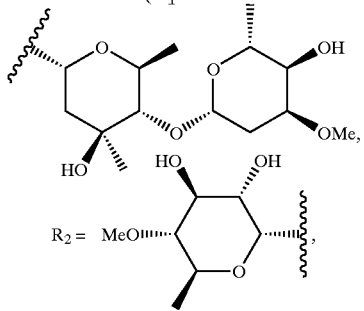

n=1, m=0).

The identity of compound of the formula I, wherein n=1 and m=0, was confirmed by NMR and mass spectrometry. High resolution FAB-MS [m/z 1165.6509 (M+Na)⁺, Δ+1.1 mmu] confirmed the molecular formula to be $C_{59}H_{98}O_{21}$. ¹³C NMR established the presence of 59 carbon atoms. ¹H NMR (500 MHz, CD₃OD) δ7.31 (s, 1H), 6.24 (s, 1H), 6.23 (s, 1H), 5.61 (m, 1H), 5.33–5.06 (m, 3H), 5.02–4.95 (m, 1H), 4.87–4.75 (m, 2H), 4.08–3.98(m, 1H), 3.82–3.78 (m, 1H), 3.80–3.70 (m, 4H), 3.59 (s, 3H), 3.56 (s, 1H), 3.51–3.16 (m, 17H), 3.05–2.98 (m, 1), 2.82–2.72 (m, 3H), 2.58–2.41 (m, 2H), 2.23–2.01 (m, 9H), 1.96–1.90 (m, 4H), 1.84–1.62 (m, 7H), 1.60–1.42 (m, 3H), 1.38–1.20 (m, 15H), 1.18–1.14 (m, 3H), 1.01–1.11 (m, 3H), 0.90–1.06 (m, 3H). No isomerization similar to that of apoptolidin to isoapoptolidin was observed at pH 7.

EXAMPLE 2

Compound of Formula I ($R_1=$

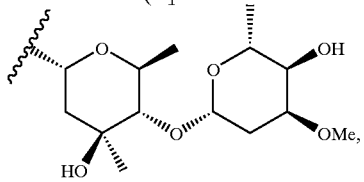

-continued

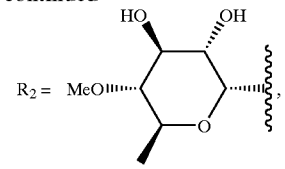

n=0, m=1).

The identity of compound of the formula I, wherein n=0 and m=1, was confirmed by NMR and mass spectrometry. High resolution FAB-MS [m/z 1165.6511 (M+Na)⁺, Δ+1.3 mmu] confirmed the molecular formula to be $C_{59}H_{98}O_{21}$. ¹³C NMR established the presence of 59 carbon atoms. ¹H NMR (500 MHz, CD₃OD) δ7.34 (s, 1H), 6.26 (s, 1H), 6.21 (s, 1H), 5.56 (m, 1H), 5.31–5.09 (m, 3H), 5.02–4.96 (m, 1H), 4.89–4.79 (m, 2H), 4.04–3.98 (m, 1H), 3.84–3.79 (m, 1H), 3.83–3.74 (m, 4H), 3.63 (s, 3H), 3.58 (s, 1H), 3.48–3.19 (m, 17H), 3.04–2.96 (m, 1), 2.82–2.72 (m, 3H), 2.56–2.42 (m, 2H), 2.28–2.01 (m, 11H), 1.94–1.90 (m, 4H), 1.80–1.60 (m, 7H), 1.60–1.44 (m, 3H), 1.37–1.22 (m, 13H), 1.18–1.13 (m, 3H), 1.03–1.11 (m, 3H), 0.88–1.06 (m, 3H). No isomerization similar to that of apoptolidin to isoapoptolidin was observed at pH 7.

EXAMPLE 3

Compound of Formula I ($R_1=$

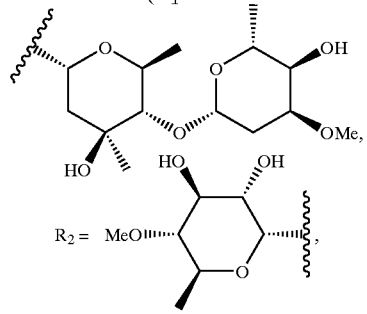

n=1, m=1).

The identity of compound of the formula I, wherein n=1 and m=1, was confirmed by NMR and mass spectrometry. High resolution FAB-MS [m/z 1179.6670 (M+Na)⁺, Δ+1.5 mmu] confirmed the molecular formula to be $C_{60}H_{100}O_{21}$. ¹³C NMR established the presence of 60 carbon atoms. ¹H NMR (500 MHz, CD₃OD) δ7.34 (s, 1H), 6.26 (s, 1H), 6.21 (s, 1H), 5.56 (m, 1H), 5.31–5.09 (m, 3H), 5.02–4.96 (m, 1H), 4.89–4.79 (m, 2H), 4.04–3.98 (m, 1H), 3.84–3.79 (m, 1H), 3.83–3.74 (m, 4H), 3.63 (s, 3H), 3.58 (s, 1H), 3.48–3.19 (m, 17H), 3.04–2.96 (m, 1), 2.82–2.72 (m, 3H), 2.56–2.42 (m, 2H), 2.28–2.01 (m, 11H), 1.94–1.90 (m, 4H), 1.80–1.60 (m, 7H), 1.60–1.44 (m, 3H), 1.37–1.22 (m, 15H), 1.18–1.13 (m, 3H), 1.03–1.11 (m, 3H), 0.88–1.06 (m, 3H). No isomerization similar to that of apoptolidin to isoapoptolidin was observed at pH 7.

EXAMPLE 4

Activity of Compounds of Formula I Against Mouse B Cell Lymphoma

Apoptosis may be readily assessed, see, for example, Kishimoto et al., J. Exp. Med., 1995, 181, 649–655; Pepper et al., Leuk Res., 1998, 22(5), 43944; and Walsh et al., J. Immunol. Methods, 1998, 217(1–2), 153–63. Accordingly, cell viability was measured by annexin and propidium iodide staning followed by FACS analysis following the manufacturer's protocol (Clontech Laboratories, Palo Alto, Calif.). The mouse B cell lymphoma cell line WEHI-231 was incubated with compounds of formula I for 8 hours, after which time the compounds were removed and the cells were stained with annexin and propidium iodide for 15 minutes and washed three times. The cells were analyzed by FACSan and the ratio of annexin positive cells was estimated. The $IC_{50}$'s of the compounds of formula I were determined and are illustrated below.

after that time at a final concentration of 0.5 mg/mL. The supernatant was discarded and the crystals were dissolved in 40 mM HCl/iPrOH. The plates were analyzed at 595 nm. The $IC_{50}$'s of the compounds of formula I were determined and are illustrated below.

| Compound of Formula I | $IC_{50}$ |
|---|---|
| $R_1$ = [disaccharide structure], $R_2$ = [sugar structure], n = 0, m = 0 | 100 nM |
| $R_1$ = [disaccharide structure], $R_2$ = [sugar structure], n = 1, m = 0 | 20 nM |
| $R_1$ = [disaccharide structure], $R_2$ = [sugar structure], n = 0, m = 1 | 150 nM |
| $R_1$ = [disaccharide structure], $R_2$ = [sugar structure], n = 1, m = 1 | 50 nM |

EXAMPLE 5

Activity of Compounds of Formula I Against Human Breast Carcinoma

Cell viability was measured by an MTT assay (Lee et al., J. Biol. Chem., 1999, 274, 13451–13455). The human breast carcinoma cell line MCF-7 was incubated with compounds of formula I for 144 hours in 96-well plates. MTT was added

| Compound of Formula I | $IC_{50}$ |
|---|---|
| $R_1$ = [disaccharide structure], $R_2$ = [sugar structure], n = 0, m = 0 | 90 nM |

-continued

| Compound of Formula I | | | IC$_{50}$ |
|---|---|---|---|
| R$_1$ = [structure] | , R$_2$ = [structure] | , n = 1, m = 0 | 30 nM |
| R$_1$ = [structure] | , R$_2$ = [structure] | , n = 0, m = 1 | 160 nM |
| R$_1$ = [structure] | , R$_2$ = [structure] | , n = 1, m = 1 | 60 nM |

We claim:

1. The compound of formula I or pharmaceutically acceptable esters, ethers, and/or salts thereof:

(I)

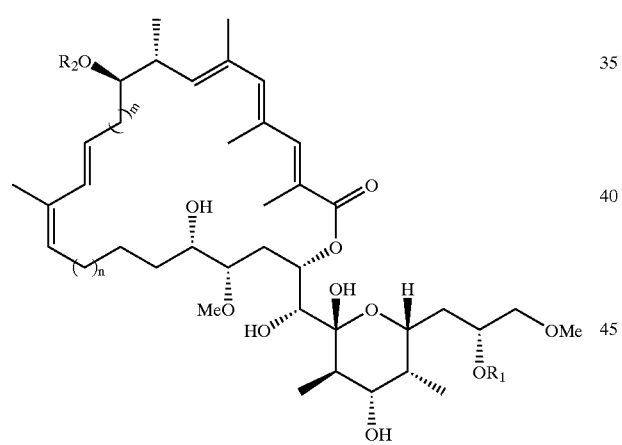

wherein:

R$_1$ is H, R, or

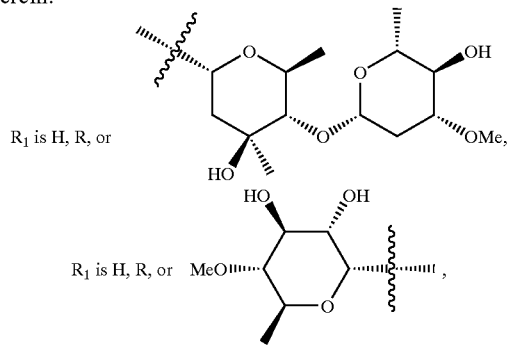

n is an integer from 0 to 6,
m is an integer from 0 to 6, except that m≠0 when n=0, and R is a substituted or unsubstituted alkyl, alkenyl, alkynyl, aryl, heterocyclyl, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio.

2. The compound of claim 1 or pharmaceutically acceptable esters, ethers, and/or salts thereof, wherein:

R$_1$ is H, or

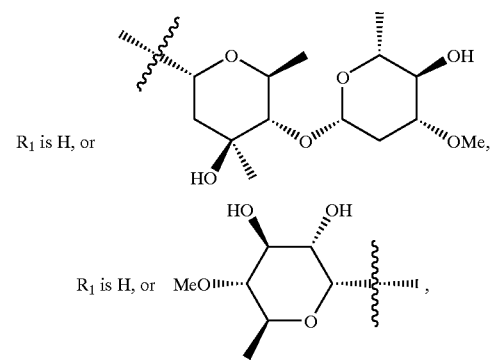

n is 0–2, and
m is 0–2, except that m≠0 when n=0.

3. The compound of claim 1 or pharmaceutically acceptable esters, ethers, and/or salts thereof, wherein:

R$_1$ is H, or

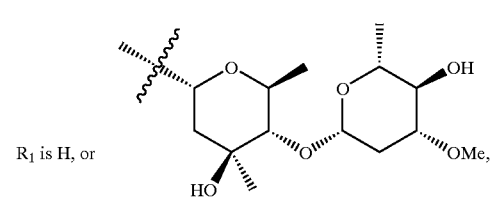

-continued

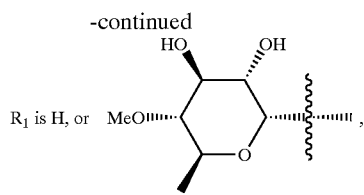

R₁ is H, or MeO n is 1–6 m is 0.

4. The compound of claim 3 or pharmaceutically acceptable esters, ethers, and/or salts thereof, wherein:

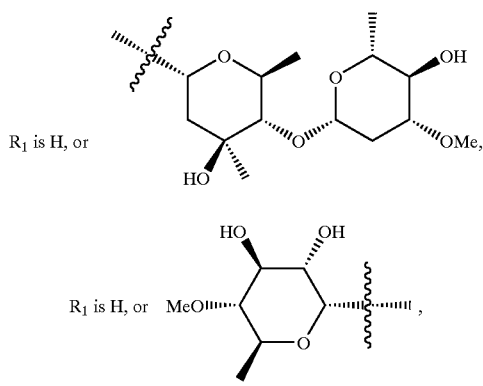

R₁ is H, or

R₁ is H, or MeO n is 1–2, and m is 0.

5. The compound of claim 4 or pharmaceutically acceptable esters, ethers, and/or salts thereof, wherein:

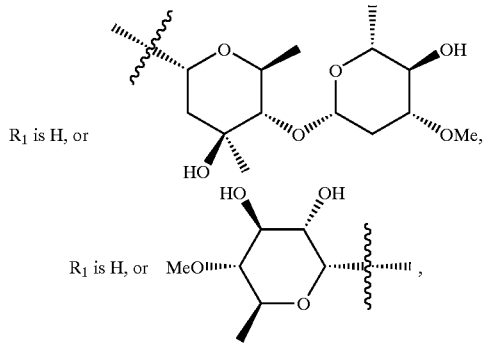

R₁ is H, or

R₁ is H, or MeO n is 1, and m is 0.

6. The compound of claim 1 or pharmaceutically acceptable esters, ethers, and/or salts thereof, wherein:

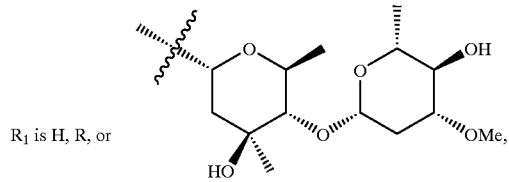

R₁ is H, R, or

-continued

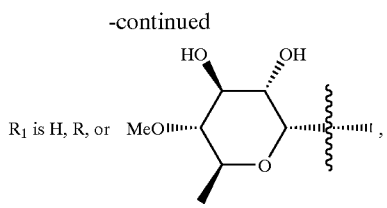

R₁ is H, R, or MeO n=0, m is 1 to 6, and

R is a substituted or unsubstituted alkyl, alkenyl, alkynyl, aryl, heterocyclyl, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio.

7. The compound of claim 6 or pharmaceutically acceptable esters, ethers, and/or salts thereof, wherein:

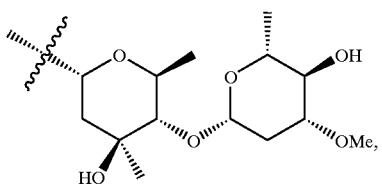

R₁ is H, or

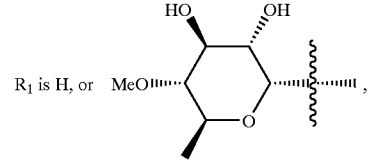

R₁ is H, or MeO n=0, and m is 1–2.

8. The compound of claim 7 or pharmaceutically acceptable esters, ethers, and/or salts thereof, wherein:

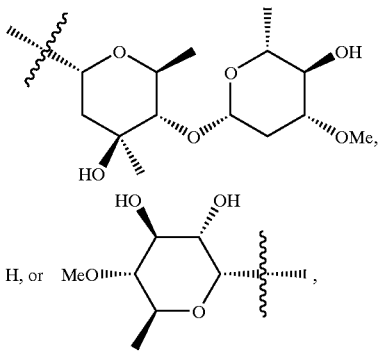

R₁ is H, or

R₁ is H, or MeO n=0, and m is 1.

9. A pharmaceutical composition comprising a pharmaceutically acceptable carrier and as active ingredient the compound of formula I

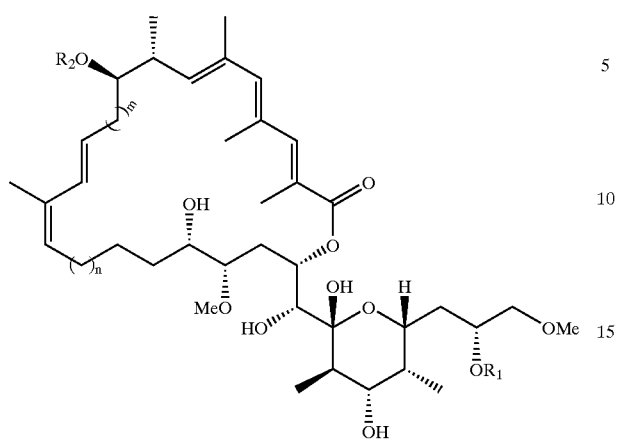

(I)

wherein:

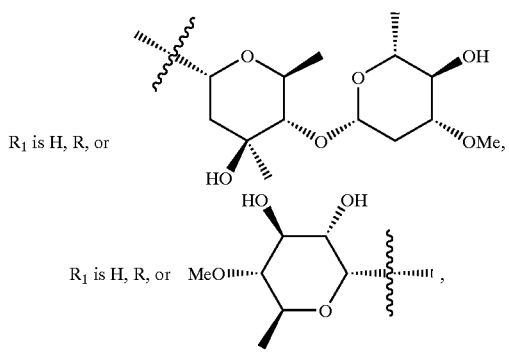

R₁ is H, R, or n is an integer from 0 to 6, m is an integer from 0 to 6, except that m≠0 when n=0, and R is a substituted or unsubstituted alkyl, alkenyl, alkynyl, aryl, heterocyclyl, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio.

10. The pharmaceutical composition of claim 9, wherein:

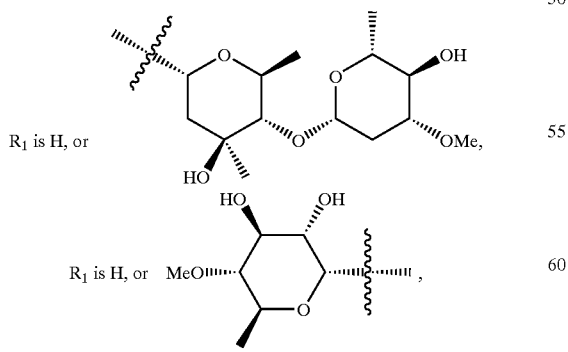

R₁ is H, or n is 0–2, and m is 0–2, except that m≠0 when n=0.

11. The pharmaceutical composition of claim 9, wherein:

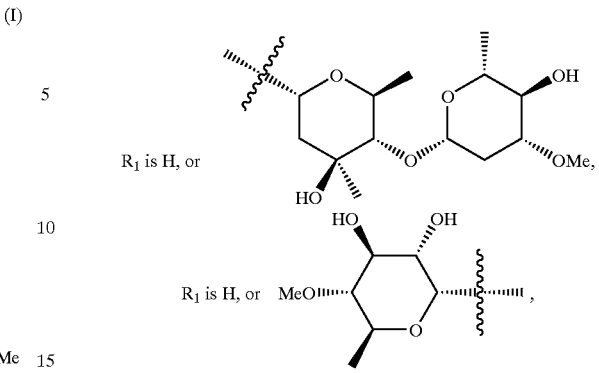

R₁ is H, or

R₁ is H, or  MeO n is 1, and m is 0.

12. The pharmaceutical composition of claim 9, wherein:

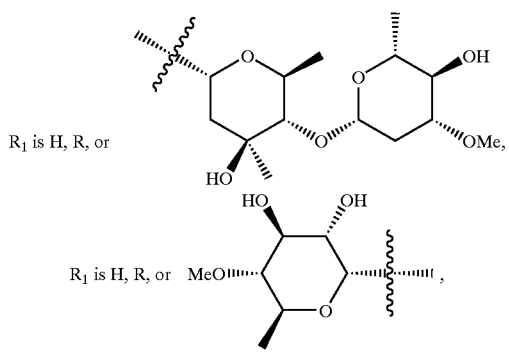

R₁ is H, R, or

R₁ is H, R, or  MeO n=0, m is 1 to 6, and

R is a substituted or unsubstituted alkyl, alkenyl, alkynyl, aryl, heterocyclyl, alkylcarbonyl, arylcarbonyl, alkoxycarbonyl, aryloxycarbonyl, aminocarbonyl, alkylcarbonyloxy, arylcarbonyloxy, aminocarbonyloxy, or alkylthio.

13. The pharmaceutical composition of claim 12, wherein:

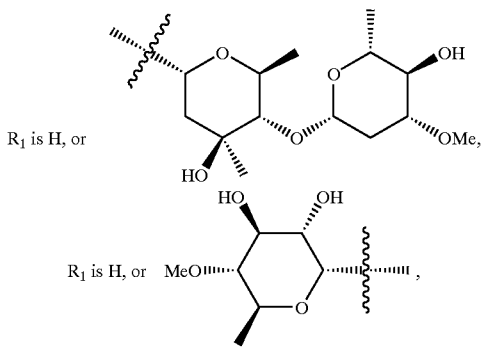

R₁ is H, or

R₁ is H, or  MeO n=0, and m is 1–2.

14. The pharmaceutical composition of claim 13, wherein:

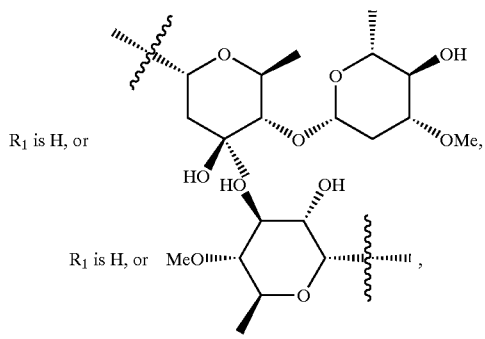

n=0, and
m is 1.

15. A method of treatment of lymphoma or breast cancer in a patient, which method comprises administering to a patient a therapeutically effective amount of the compound of claim 1.

16. A method of treatment of a lymphoma or breast cancer in a patient, which method comprises administering to a patient a therapeutically effective amount of the composition of claim 9.

17. The method of claim 16, wherein the lymphoma is one of: B-cell lymphoma, T-cell-lymphoma, Hodgkin's lymphoma, non-Hodgkin's lymphoma, hairy cell lymphoma or Burkett's lymphoma.

* * * * *